(12) United States Patent
Cohen-Daniel

(10) Patent No.: US 11,715,552 B2
(45) Date of Patent: Aug. 1, 2023

(54) MEDICINE DISPENSER

(71) Applicant: Zion Cohen-Daniel, Beer Yaakov (IL)

(72) Inventor: Zion Cohen-Daniel, Beer Yaakov (IL)

( * ) Notice: Subject to any disclaimer, the term of this patent is extended or adjusted under 35 U.S.C. 154(b) by 142 days.

(21) Appl. No.: 17/404,101

(22) Filed: Aug. 17, 2021

(65) Prior Publication Data

US 2021/0375420 A1 Dec. 2, 2021

Related U.S. Application Data

(63) Continuation-in-part of application No. 16/655,279, filed on Oct. 17, 2019, now abandoned.

(60) Provisional application No. 62/790,480, filed on Jan. 10, 2019.

(51) Int. Cl.
*G16H 20/13* (2018.01)
*G06K 7/14* (2006.01)
*G07F 17/00* (2006.01)

(52) U.S. Cl.
CPC ........... *G16H 20/13* (2018.01); *G06K 7/1413* (2013.01); *G07F 17/0092* (2013.01)

(58) Field of Classification Search
CPC ..... G07F 17/0092; G16H 20/13; A61J 7/0069
See application file for complete search history.

(56) References Cited

U.S. PATENT DOCUMENTS

| | | | |
|---|---|---|---|
| 6,711,460 B1* | 3/2004 | Reese | G16H 20/10 700/216 |
| 2009/0188937 A1* | 7/2009 | Kim | A61J 7/0069 221/312 B |
| 2010/0030374 A1* | 2/2010 | Saltsov | A61J 7/0481 700/231 |

* cited by examiner

*Primary Examiner* — Timothy R Waggoner
(74) *Attorney, Agent, or Firm* — Alphapatent Associates, Ltd; Daniel J. Swirsky

(57) ABSTRACT

A medicine dispenser, including a medicine prescription reader, for reading a medicine prescription including two due times, trays, each for containing medicine doses of one type only, and a robot, for dispensing medicine doses from at the trays to two cells of box according to the reading of the medicine prescription reader, thereby dedicating each of the cells to one of the due times.

5 Claims, 3 Drawing Sheets

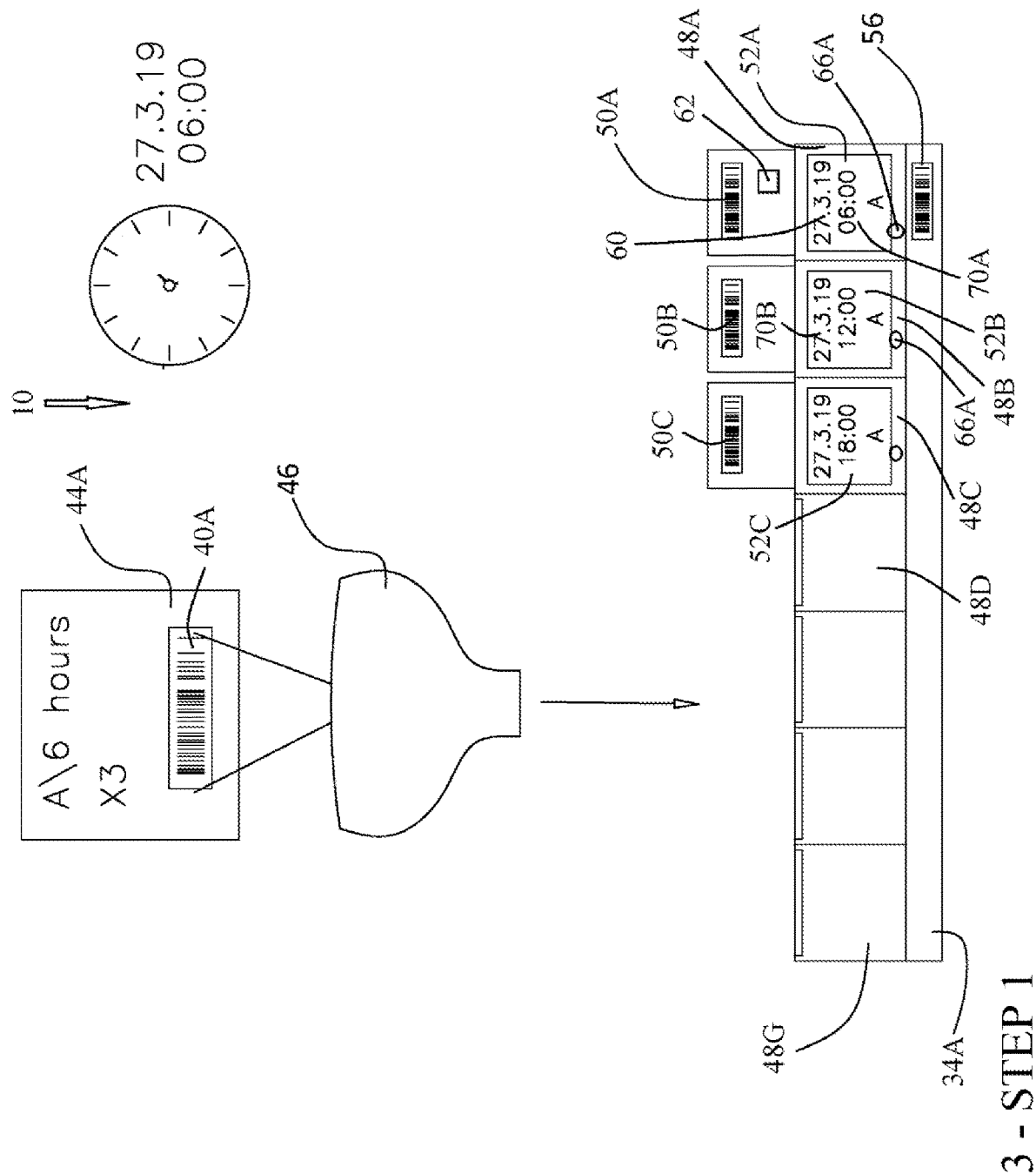
FIG 3 - STEP 1

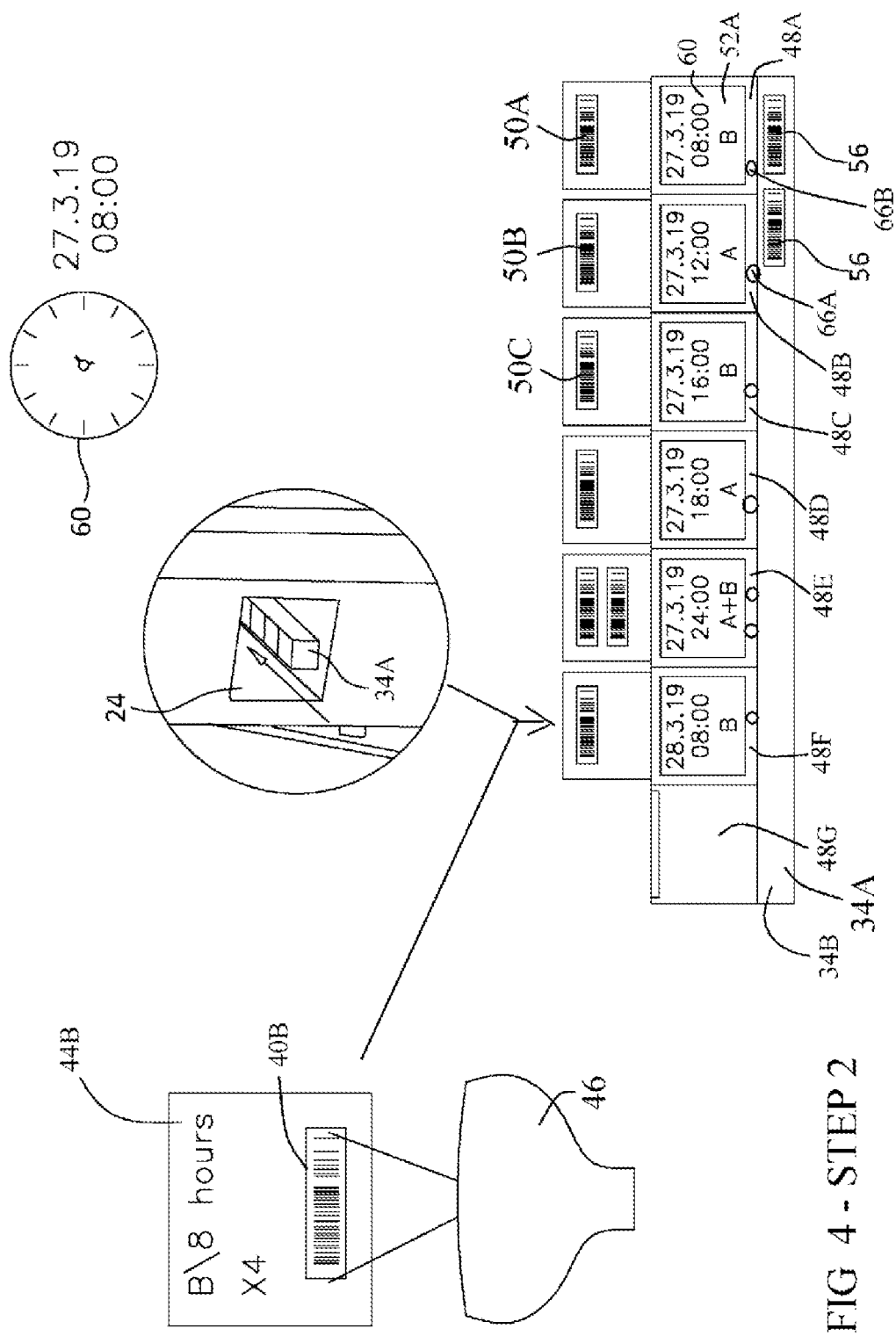
FIG 4 - STEP 2

MEDICINE DISPENSER

CROSS-REFERENCE TO RELATED APPLICATIONS

This application is a Continuation-in-Part of U.S. patent application Ser. No. 16/655,279, filed Oct. 17, 2019, which claims the benefit of priority from U.S. Provisional Patent Application No. 62/790,480, filed Jan. 10, 2019, the disclosures of which are incorporated herein by reference.

FIELD

The invention relates to the field of medical prescriptions and medicine provision.

BACKGROUND

Issue of medicines, storage and sale of drugs constitute an expensive logistical process and is not always available according to the needs of the patient. The drug identification process is done in a way that is not sufficiently safe.

U.S. Pat. No. 6,711,460 to Reese teaches multitasking where a single robot prepares two prescriptions, as taught: In this exemplary embodiment the tasks necessary to prepare prescriptions or other orders are split between two separate vaults, and performed in part by each of two separate robots. In other embodiments all of these tasks may be performed by a single robot in a single vault. In further embodiments, these tasks may be split differently, or may be accomplished in more than two vaults or by more than a single robot in each of one or more vaults.

US 2010/003030374 to Saltsov teaches inserting an empty box 30, as taught: An empty four quadrant pill box is placed in the device in the load position and the device then receives, moves and rotates the pill box to the appropriate positions.

US 2009/0188937 to Kim teaches an inlet for a box.

There is a long felt need to provide a solution to the above-mentioned and other problems of the prior art.

SUMMARY

A medicine dispenser, including a medicine prescription reader, trays, each for containing medicine doses of one type, and a robot, for dispensing medicine doses to the cells.

BRIEF DESCRIPTION OF THE DRAWINGS

Embodiments, features, and aspects of the invention are described herein in conjunction with the following drawings, in which:

FIG. 3 describes the input and output of the medicine dispenser of FIG. 1 at a first step; and FIG. 4 describes the input and output of the medicine dispenser of FIG. 1 at a second step.

The drawings are not necessarily drawn to scale.

DETAILED DESCRIPTION

The invention will be understood from the following detailed description of embodiments of the invention, which are meant to be descriptive and not limiting. For the sake of brevity, some well-known features are not described in detail.

The reference numbers have been used to point out elements in the embodiments described and illustrated herein, in order to facilitate the understanding of the invention. They are meant to be merely illustrative, and not limiting. Also, the foregoing embodiments of the invention have been described and illustrated in conjunction with systems and methods thereof, which are meant to be merely illustrative, and not limiting.

Figure 1:
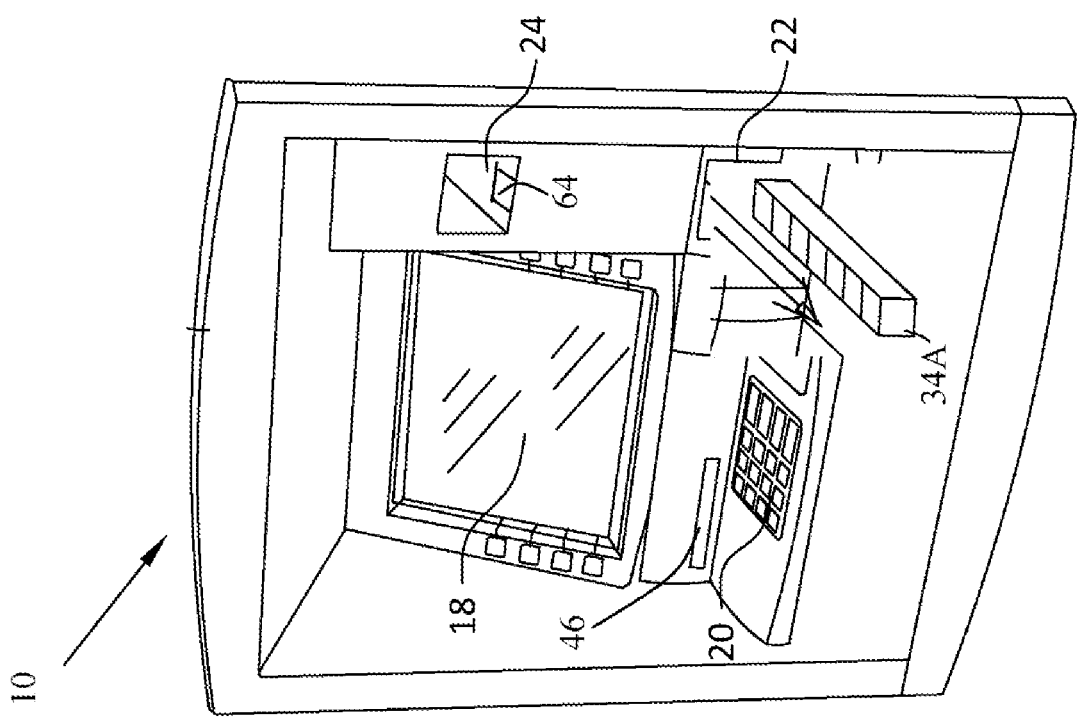
FIG. 1 is a medicine dispenser according to one embodiment, from the client's side.

FIG. 1 is a medicine dispenser according to one embodiment, from the client's side.

Figure 2:
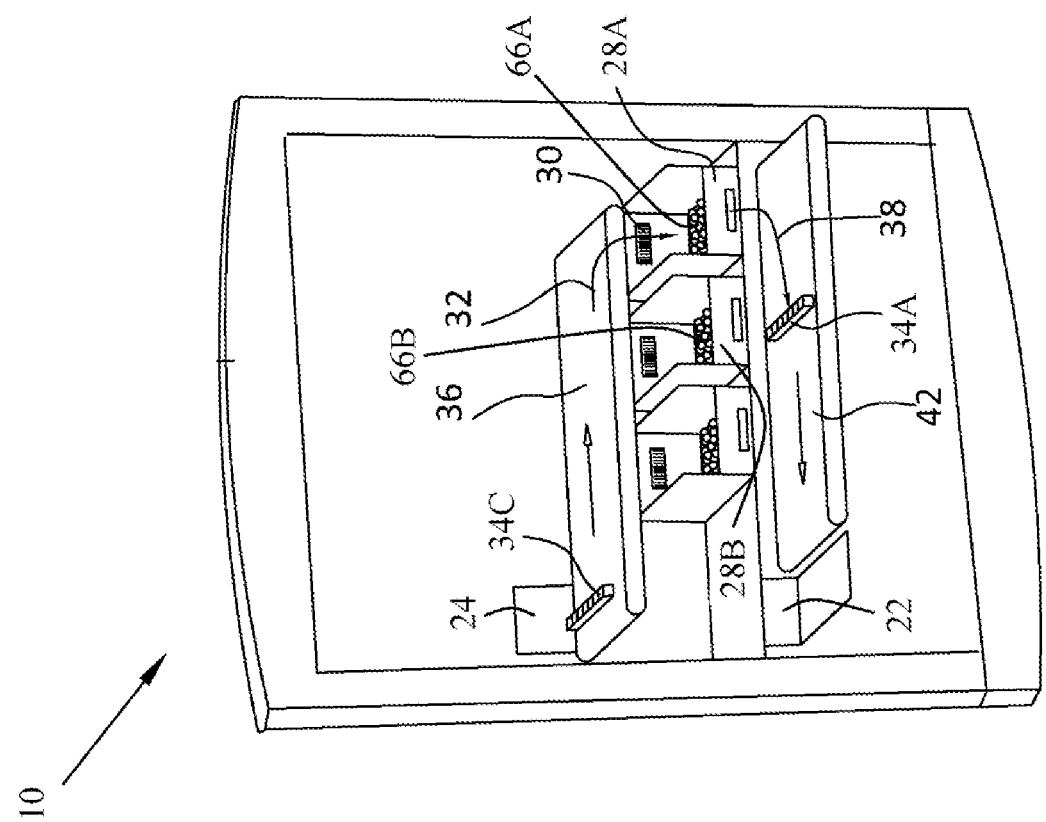
FIG. 2 is the medicine dispenser of FIG. 1 from the pharmacist side.

FIG. 2 is the medicine dispenser of FIG. 1 from the pharmacist side.

A client may provide a medicine prescription, and receive a medicine box 34A from outlet 22 of a medicine dispenser 10 according to one embodiment.

According to one embodiment, the client may further provide a medicine box 34C, for receiving medicine box 34A, considering medicine box 34C.

The term "medicine dose" refers herein to any medicine for being completely consumed at a certain time, such as a pill, tablet, liquid dose, etc.

Medicine dispenser 10 transfers medicine doses of medicine box 34C into medicine trays 28A, 28B, etc., as shown by arrow 32; and transfers from medicine doses from medicine trays 28A, 28B, etc. into medicine box 34A, as shown by arrow 38.

FIG. 3 describes the input and output of the medicine dispenser of FIG. 1 at a first step.

FIG. 3 depicts an example of a barcode reader 46 of medicine dispenser 10 reading at the first step, being at 6:00 o'clock of date 27/3/19, a barcode 40A of medicine prescription 44A, instructing to dispense 3 medicine doses of type A one per 6 hours.

Accordingly, medicine dispenser 10 dispenses medicine box 34A, including a plurality of cells, of which cells 48A, 48B and 48C contain medicine of type A, and cells 48D to 48G are empty.

For example, tray 28A may include 10 liters of liquid medicine, and cell 48A containing medicine of type A may include 5 milliliters from tray 28A being sterilely packaged.

Medicine dispenser 10 further stamps user readable instructions 60 explaining barcode 40A of medicine prescription 44A to each of cells 48A, 48B and 48C, such as by sticking stickers 52A, 52B and 52C.

According to the due times example of 3 medicine doses of type A one per 6 hours, sticker 52A of cell 48A may indicate medicine A at due time 70A of 6 o'clock; sticker 52B of cell 48A may indicate medicine A at a due time 70B of 12 o'clock; and sticker 52C of cell 48C may indicate medicine A at 18 o'clock.

Sticker 52A may further include a barcode 50A including the information of cell 48A, such as user readable instructions 60 of cell 48A; sticker 52A may include a barcode 50B for cell 48B; and sticker 52C may include a barcode 50C for cell 48C.

Barcodes 50A, 50B and 50C may include visual and/or vocal gadgets 62, for alerting the information thereof. For example, a bulb 62 of barcode 50A may blink at 6 o'clock.

FIG. 4 describes the input and output of the medicine dispenser of FIG. 1 at a second step.

At the second step, being after consuming the first medicine dose of type A of medicine box 34A, FIG. 4 depicts an example of barcode reader 46 reading at 8:00 o'clock of date 27/3/19, a new medicine prescription 44B including a new barcode 40B, instructing to dispense 4 medicine doses of type B one per 8 hours.

FIG. 4 further depicts that the user decides to return medicine box 34A.

Referring again to FIG. 1, inlet 24 of medicine dispenser 10 includes a barcode reader 64, thereby reading barcodes 50A, 50B and 50C, thus knowing the physical contents of medicine box 34A, which was filled by prescription 44A (FIG. 3).

Referring again to FIG. 4, accordingly, medicine dispenser 10 fills medicine box 34A or a new medicine box 34B containing medicines considering the combination of barcodes 40A and 40B and considering the partial consumption of medicine prescription 44A of box 34A according to the consumption instructed by barcode 40A of medicine prescription 44A of FIG. 3, which has provided box 34A; and dispenses medicine box 34A or 34B to outlet 22.

Thus, and considering the first medicine dose of type A of medicine prescription 44A of medicine box 34A has been consumed, cell 48A of dispensed medicine box 34A or 34B contains a medicine dose of type B; cell 48B of dispensed medicine box 34A or 34B contains a medicine dose of type A; cell 48C contains a medicine dose of type B; cell 48D contains a medicine dose of type A; cell 48E contains one medicine dose of type A and another medicine dose of type B; cell 48F contains one medicine dose of type B; and cell 48G is empty.

Medicine dispenser 10 further stamps user readable instructions 60 explaining the combination of barcodes 40A and 40B of medicine prescriptions 44A and 44B to each of the cells.

Thus, in this case, the sticker 52A of cell 48A indicates medicine B at 8 o'clock of date 27/3/19; cell 48B indicates medicine A at 12 o'clock; cell 48C indicates medicine B at 16 o'clock; cell 48D indicates medicine A at 18 o'clock; cell 48E indicates medicines A and B at 24 o'clock, yet of date 27/3/19; and cell 48F indicates medicine B at 8 o'clock of date 28/3/19, thus providing artificial intelligence.

Trays 28A, 28B, etc., cells 48A, 48B, etc. and robot 36 may be sterilized, for providing sterilized dispensing from mass packaging to personal packaging.

The medicine dispenser includes inlet 24 and outlet 24, in that after dispensing box 34A of prescription 44A from outlet 22, and after partly consuming from box 34A according to prescription 44A, the user may insert box 34A into inlet 24 to allow the machine to dispense medicine doses into box 34A according to prescription 34A and considering the partial consumption, and further according to a new prescription 34B.

Box 34A will include doses of the combination of prescriptions 44A and 44B, while considering that box 34A has been partly consumed according to prescription 44A prior to the insertion of box 34A into inlet 24.

The medicine dispenser fills the box using a combination of or other relation between, the two prescriptions, and preparation of a single box and single cell thereof accommodating at least two prescriptions.

Thus, in one aspect the invention is directed to a medicine dispenser, including:
- a medicine prescription reader, for reading at least first (44A) and second medicine prescriptions including at least two due times;
- a plurality of trays, each for containing medicine doses of one type only;
- a robot, for dispensing medicine doses from at least one of the trays into at least two cells of a box, according to the reading of the first medicine prescription by the medicine prescription reader, thereby dedicating each of the at least two cells to one of the at least two due times;
- an outlet for dispensing the box after the dispensing of the medicine doses thereinto; and
- an inlet for inserting the box after the medicine doses dispensing thereinto and after been dispensed from the outlet and after been partly consumed according to the first prescription,
- where the robot is further configured to dispense medicine doses from the at least one of the trays to the box upon the receipt, according to the combination of the first (44A) and second medicine prescriptions while considering the partial consumption of the first prescription (44A).

The medicine dispenser (10) may include:
- a medicine prescription reader (46), for reading a medicine prescription (44A) including due times (70A,70B);
- trays (28A,28B), each for containing medicine doses of one type only;
- a robot (36), for dispensing medicine doses (66A) from at the trays (28A) to cells (48A,48B) of box (34A), according to the reading of the medicine prescription reader (46),
- thereby dedicating each (48A) of the cells to one (70A) of the due times.

The trays (28A,28B), the cells (48A,48B) of the box (34A), and the robot (36) may be sterilized, thereby providing sterilized dispensing from mass packaging of the trays (28A,28B) to personal packaging of the box (34A).

The dedicating of each (48A) of the cells to one (70A) of the due times, may include presentations (60) disposed on the first box (34A) of at least the due times (70A).

The presentations (60) disposed on the first box (34A) of at least the due times (70A) may constitute alerts (62).

The medicine dispenser (10) may further include a barcode reader (64), wherein the presentations (60) disposed on the box (34A) of at least the due times (70A) may include a barcode (50A), for being readable by the barcode reader (64).

The first medicine prescription (44A) may include the first medicine prescription (44A) and a second medicine prescription (44B), thereby the dispensing is according to a combination of the first (44A) and second (44B) medicine prescriptions.

The medicine dispenser (10) may further include an inlet (24), for receiving a second box (34B) including the medicine doses (66A) dispensed according to the second medicine prescription (44B), thereby dispensing according to the second medicine prescription (44B) more than one time.

In the figures and/or description herein, the following reference numerals (Reference Signs List) have been mentioned:
- numeral 10 denotes the medicine dispenser according to one embodiment of the invention;
- 18: display;
- 20: keyboard;
- 22: outlet;
- 24: inlet;
- 28A,28B: medicine trays;
- 30: barcode indicating type of medicines in tray 28A;
- 32: arrow;
- 34A,34B,34C: boxes dispensed by medicine dispenser 10, each including a plurality of cells;
- 36: robot including a conveyor;
- 38: arrow;

40A,40B: barcodes including information of prescriptions;
42: arrow;
44A,44B: medicine prescriptions;
46: medicine prescription reader, which may read a printed or an electronic sheet;
48A,48B,48C,48D,48E,48G: cells of dispensed box 34A;
50A,50B,50C: barcodes describing the information of dispensed box 34A; each may describe the information of one cell;
52A,52B,52C: stickers;
56: a single barcode describing the entire contents of box 34A;
60: instructions/presentations attached to dispensed box 34A, such as stickers 52A readable to the user and/or being alerts to the user and/or being barcodes 50A readable to medicine dispenser 10, for re-dispensing its contents as a combination with another box;
62: bulb or loudspeaker for alerting; each bulb may alert a certain cell to consume from;
64: barcode reader;
66A,66B: medicine doses, each of another type;
70A,70B: due time for consuming a dose;

The foregoing description and illustrations of the embodiments of the invention have been presented for the purpose of illustration, and are not intended to be exhaustive or to limit the invention to the above description in any form.

Any term that has been defined above and used in the claims, should to be interpreted according to this definition.

The reference numbers in the claims are not a part of the claims, but rather used for facilitating the reading thereof. These reference numbers should not be interpreted as limiting the claims in any form.

What is claimed is:

1. A medicine dispenser, comprising:
a medicine prescription reader, for reading at least a first medicine prescription and a second medicine prescription comprising at least two due times;
a plurality of trays, each of said plurality of trays containing medicine doses of one type only;
a robot, for dispensing said medicine doses from at least one of said plurality of trays into at least two cells of a box, according to said reading of said first medicine prescription by said medicine prescription reader, thereby dedicating each of said at least two cells to one of said at least two due times;
an outlet for dispensing said box after dispensing of said medicine doses thereinto; and
an inlet for inserting said box after dispensing said medicine doses thereinto and after said box has been dispensed from said outlet and after said medicine doses in said box have been partly consumed according to said first prescription,
wherein said robot is further configured to said dispense medicine doses from at least one of said plurality trays upon said inserting of said box, according to a combination of said first medicine prescription and said second medicine prescription while considering a partly consumed state of said first prescription.

2. The medicine dispenser according to claim 1, wherein said plurality of trays, said at least two cells of said box, and said robot are sterilized, thereby providing sterilized dispensing from mass packaging of said trays to personal packaging of said box.

3. The medicine dispenser according to claim 1, wherein said dedicating of each of said at least two cells to one of said at least two due times, comprises presentations disposed on said box of at least said due times.

4. The medicine dispenser according to claim 3, wherein said presentations disposed on said box of at least said due times comprise alerts.

5. The medicine dispenser according to claim 3, further comprising a barcode reader, wherein said presentations disposed on said box of at least said due times comprise at least one barcode, for being readable by said barcode reader.

* * * * *